United States Patent
Campbell et al.

[19]

[11] Patent Number: 5,843,171
[45] Date of Patent: Dec. 1, 1998

[54] METHOD OF INSITU BYPASS TO HOLD OPEN VENOUS VALVES

[75] Inventors: Carey V. Campbell, Flagstaff; James H. Chastain, Cottonwood; Larry J. Kovach, Flagstaff; Alvaro J. Laguna, Flagstaff; Daniel B. Pond, Flagstaff, all of Ariz.

[73] Assignee: W. L. Gore & Associates, Inc., Newark, Del.

[21] Appl. No.: 788,628

[22] Filed: Jan. 24, 1997

Related U.S. Application Data

[63] Continuation-in-part of Ser. No. 592,912, Jan. 29, 1996, Pat. No. 5,747,128.

[51] Int. Cl.$^6$ ........................................... A61F 2/06
[52] U.S. Cl. ............................... 623/1; 623/12; 606/198; 600/29
[58] Field of Search ...................... 623/1, 2, 12; 606/191, 606/195, 198; 600/29, 30, 31

[56] References Cited

U.S. PATENT DOCUMENTS

| | | |
|---|---|---|
| 3,626,947 | 12/1971 | Sparks ........................................ 623/1 |
| 4,208,745 | 6/1980 | Okita . |
| 4,248,924 | 2/1981 | Okita . |
| 4,280,500 | 7/1981 | Ono . |
| 4,332,035 | 6/1982 | Mano . |
| 4,550,447 | 11/1985 | Seiler, Jr. et al. . |
| 4,647,416 | 3/1987 | Seiler, Jr. et al. . |
| 4,701,362 | 10/1987 | Suzuki et al. . |
| 4,730,088 | 3/1988 | Suzuki . |
| 4,877,661 | 10/1989 | House et al. . |
| 5,026,513 | 6/1991 | House et al. . |
| 5,308,664 | 5/1994 | House et al. . |
| 5,443,909 | 8/1995 | Martakos et al. . |
| 5,466,509 | 11/1995 | Kowligi et al. . |
| 5,474,824 | 12/1995 | Martakos et al. ........................... 623/1 |
| 5,476,505 | 12/1995 | Limon ........................................ 623/1 |
| 5,609,626 | 3/1997 | Quijano et al. ............................. 623/1 |

FOREIGN PATENT DOCUMENTS

| | | |
|---|---|---|
| 0775472 | 5/1997 | European Pat. Off. . |
| 8403036 | 8/1984 | WIPO ....................................... 623/1 |
| 9510247 | 4/1995 | WIPO . |
| 9600103 | 1/1996 | WIPO . |
| 9633066 | 10/1996 | WIPO . |

OTHER PUBLICATIONS

SRRT Thin Walled FEP Ringed GORE–TEX® Stretch Vascular Graft with Removable Rings Product Brochure. W. L. Gore & Associates, Inc. 1995.

(List continued on next page.)

*Primary Examiner*—Paul B. Prebilic
*Attorney, Agent, or Firm*—Wayne D House

[57] ABSTRACT

A tube of porous PTFE having at least two first and at least two second regions wherein the at least two first regions have a greater density than the at least two second regions. For tubes of porous expanded PTFE having a microstructure of nodes interconnected by fibrils, the at least two first regions have a mean fibril length that is less than that of the at least two second regions. Preferably the regions are arranged in the form of ring-shaped segments of the tube wherein denser segments alternate along the length of the tube with less dense segments. Other arrangements between the different regions are possible; for example, the regions may be oriented in a spiral relationship with each other along the length of the tube. The porous PTFE tubes of the present invention have excellent radial compression resistance without requiring additional exterior reinforcing members due to the presence of the denser regions that are provided with a circumferential orientation. Tubes of this type are anticipated to be useful as vascular grafts and particularly as intraluminal vascular grafts. When provided as an intraluminal graft, the tube may also optionally be manufactured to be circumferentially distensible to a larger diameter up to a maximum diameter beyond which it will not distend during normal use; such a tube can also be made to recoil minimally on the release of the distending force. The tube may be used in in situ bypass procedures to hold venous valves open and to occlude tributary branches.

4 Claims, 6 Drawing Sheets

OTHER PUBLICATIONS

Rosenfeld JC et al. Endothelial Infiltration and Lining of Knitted Dacron Arterial Grafts. Surgical Forum 1981; 132:336–38.

Onuki Y et al. Accelerated Enothelialization Model For The Study Of Dacron Graft Healing. Annals of Vasc Surgery 1997; 11:141–48.

Graham L M et al. Enhanced Endothelialization of Dacron Grafts By External Vein Wrapping. Journal of Surgical Research 1995; 38:537–45.

Bull D A et al. Cellular Origin and Ratoe of Endothelial Cell Coverage of PTFE Grafts. Journal of Surgical Research 1995; 58:58–65.

Sterpetti A V. Healing of High–Porosity Polytetrafluoroethylene Arterial Grafts Is Influenced By The Nature Of The Surrounding Tissue. Surgery 1992; 111:667–82.

Lepidi S. The Degree of Porosity Influences The Release of Growth Factors By Healing Polytetrafluoroethylene(PTFE) Grafts. European Journal of Vascular Surgery 1996; 11:36–41.

Sedlairk K M et al. Rapid Endothelialization of Microporous Vascular Prostheses Covered With Meshed Vascular Tissue: A Preliminary Report. Biomaterials 1990; 11:4–7.

Holubee H et al. The Relationship Between PTFE Graft Ultrastructure and Cellular Ingrowth: The Influence Of An Autologous Jugular Vein Wrap. Biomaterials Mechanical Properties 1994; 53–64.

Ahn S S et al. Endovascular Femoropopliteal Bypass: Early Human Cadaver and Animal Studies. Ann Surg 1995; 9:28–36.

Dolmatch B L et al. Patency and Tissue Response Related to Two Types of Polytetrafluoroethylene–Covered Stents in the Dog. Journal of Vascular and Interventional Radiology. 1996; 641–49.

Morris G E et al. Endovascular Femoropopliteal Bypass: A Cadaveric Study. Eur J Vasc Endovasc Surg 1995; 10:9–15.

Martin M L et al. Human transluminally placed endovascular stentedgrafts: Preliminary histopathologic analysis of healing grafts in aortoiliac and femoral artery occlusive disease. J Vasc Surg 1995; 21:595–604.

Parodi J C. Endovascular Repair of Abdominal Aortic Aneurysms and Other Arterial Lesions. J Vasc Surg 1995; 21:549–57.

Dake M D et al. Transluminal Placement of Endovascular Stent–Grafts For The Treatment of Descending Thoracic Aortia Aneuryms. New England Journal of Medicine 1994; 331:1729–34.

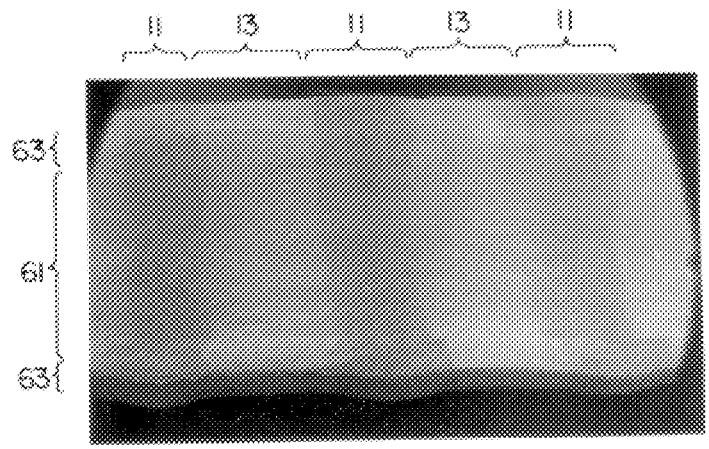
FIG. 6   x12
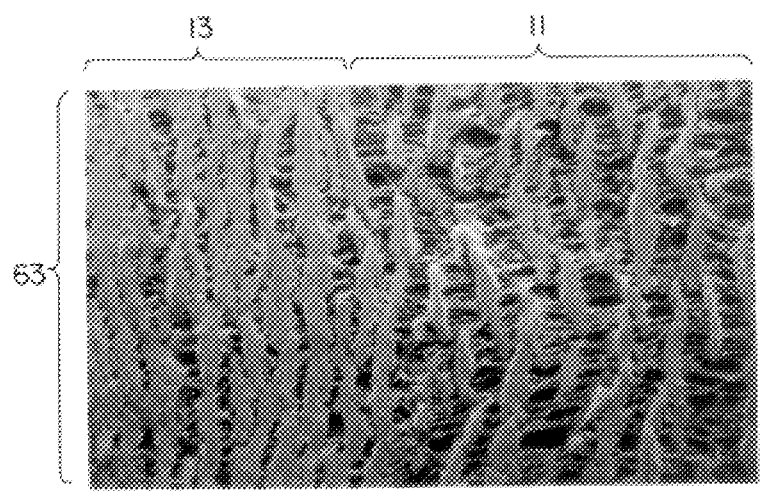
FIG. 7A   x500
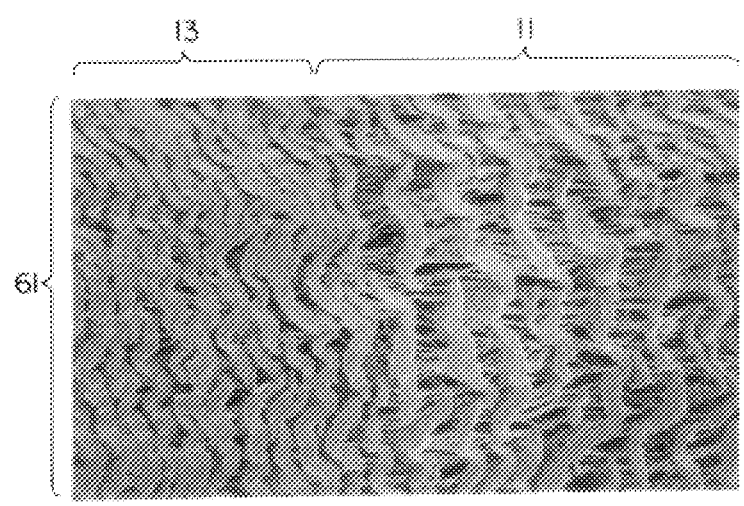
FIG. 7B   x500

METHOD OF INSITU BYPASS TO HOLD OPEN VENOUS VALVES

RELATED APPLICATIONS

The present application is a Continuation-in-Part of U.S. patent application Ser. No. 08/592,912 filed Jan. 29, 1996 now U.S. Pat. No. 5,747,128.

FIELD OF INVENTION

This invention relates to the field of prosthetic vascular grafts.

BACKGROUND OF THE INVENTION

There exists a need for a vascular graft with radial support to withstand external compressive forces to be used in various vascular grafting applications including bypass grafts and intraluminal grafts. Bypass grafts are surgically implanted to bypass diseased segments of natural vessels. Intraluminal grafts are implanted inside natural vessels or grafts. A radially supported graft that additionally possesses circumferential distensibility affords the vascular surgeon more options in correctly sizing the graft for the patient's needs. That is, the surgeon can use a balloon catheter to increase the circumference of the graft to a desired diameter; the surgeon can even create a tapered section should he or she so desire. A balloon catheter or other pressurization means can be utilized to increase the circumference of an intraluminal graft within a host vessel thereby maximizing the available flow area. The ends of the graft can be affixed to the host vessel or previously implanted vascular graft by known mechanical fastening means; in some instances in intraluminal grafting it may not require fastening, particularly at the downstream (distal) end.

Such a graft has even greater value if it possesses kink resistance and has minimal diametrical recoil subsequent to increasing the graft circumference. These attributes further enhance the ability of the graft to remain patent since reduction in flow cross sectional area adversely affects patency.

Various published documents describe the use of porous polytetrafluoroethylene (hereinafter PTFE) vascular grafts with external reinforcement for blood conduits. Fluorinated ethylene propylene (FEP) rings and spiral beading of PTFE attached to the exterior surface of PTFE grafts have long been commercially available. External support has also been applied to other types of vascular grafts, specifically polyethylene terephthalate (PET) grafts.

Various published documents also describe the intraluminal use of porous PTFE vascular grafts. See, for example Ahn, SS et al., "Endovascular Femoropopliteal Bypass: Early Human Cadaver and Animal Studies,"Ann Surg 1995; 9:28–36; Morris, GE et al., "Endovascular Femoropopliteal Bypass: A Cadaveric Study," Eur J Vasc Endovasc Surg 1995; 10:9–15; and Marin, ML et al., "Human Transluminally Placed Endovascular Stented Grafts: Preliminary Histopathologic Analysis of Healing Grafts in Aortoiliac and Femoral Artery Occlusive Disease,"J Vasc Surg 1995; 21:595–604.

External reinforcement tends to be rigid and may leave sharp edges when the graft is cut to the appropriate length. Furthermore, the rigidity of the member and the exterior placement of the reinforcement may cause erosion of the surrounding tissues. External reinforcement may make it more difficult to implant or retrieve a vascular graft. Also, these means of external reinforcement prohibit the ability to increase the circumference of the graft in the supported regions.

The literature describes various PTFE materials which may be used as vascular grafts or various other medical devices. U.S. Pat. No. 4,280,500 to Ono describes a tubular flexible medical instrument in the form of a catheter introducer comprising a tube of longitudinally alternating segments of porous and solid PTFE. While such a tube has good flexibility and substantial radial compression resistance, it is an unlikely material for use as a vascular graft because it contains solid (non-porous) material at the inner surface of the tube.

Seiler et al., describe a PTFE vascular graft having external reinforcing structures made by transversely scoring the exterior surface of a porous PTFE tube. The scoring is performed either before or after stretching and is accomplished with, for example, a sharp blade inserted part of the way through the wall of a tube from the exterior surface of the tube. If scored prior to stretching, the subsequent stretching step separates the material between the scores which then substantially retains the higher density of the unstretched material while the remainder of the tube (the inner portion) becomes more porous during stretching. The denser portions at the exterior of the tube between the transverse scores forms external reinforcing structures. Alternatively, the scoring can be accomplished after the tube is stretched, in which case it is subsequently heated above the melt temperature of PTFE while being longitudinally restrained, causing the material between scores to shrink and form denser, exterior reinforcing structures.

Various other patents related to porous expanded PTFE describe materials having varying microstructures. For example, U.S. Pat. Nos. 4,208,745 and 4,248,924 to Okita describe porous expanded PTFE vascular grafts and film materials having asymmetrical microstructures wherein one surface of the material has a substantially different average pore size or fibril length than the opposing surface. U.S. Pat. No. 4,332,035 to Mano describes a porous PTFE material having predominant strength orientations of the opposing surfaces in directions at right angles to each other.

Suzuki teaches in U.S. Pat. Nos. 4,701,362 and 4,730,088 a method of forming holes into or entirely through porous PTFE sheet materials with the use of a laser whereby the material around the perimeter of the formed holes is made non-porous. The resulting perforated sheet material has reinforced holes and is described as being a compression resistant material useful for various electronics applications such as a dielectric insulating material.

In U.S. Pat. Nos. 4,877,661; 5,026,513 and 5,308,664, House and Myers describe a porous PTFE material having bent fibrils which provide the material with the ability to stretch and recover repeatedly. When made in tubular form as a vascular graft, the resulting tube exhibits stretch behavior in the direction of the length of the tube. Tubes of this type are also kink-resistant during bending and have slightly more compression resistance than a conventional porous expanded PTFE tube, however they are not adequately compression resistant in the sense of being able to resist external compressive forces which may result from particular implant situations such as implants that extend across joints for which grafts having external ring or spiral reinforcements are conventionally employed.

U.S. Pat. No. 5,466,509 to Kowligi et al., teaches a method of providing porous PTFE materials having internodal distances varying over relatively wide ranges by impressing or forming patterns into PTFE extrudate prior to the stretching step typically used to create porous expanded PTFE. This process is described as a method of increasing the porosity of porous PTFE without impairing its other mechanical properties.

SUMMARY OF THE INVENTION

The present invention is a vascular graft possessing internal radial support as opposed to an additional external member. Such a construction can be expected to obviate the problems associated with external support.

The present invention is a vascular prosthesis with internal radial support to resist external compressive forces. No additional materials are required to be added to the graft to provide the internal support. Rather, the graft is compressed longitudinally to increase its density and regions along the length are heated to preserve the increase in density. This process provides alternating regions of higher and lower densities and corresponding variations in rigidity along the length of the graft. The alternating regions can be characterized by the attendant alternating fibril lengths in the regions, with the denser regions having shorter mean fibril lengths.

The regions are considered to lie between the exterior and luminal surfaces of the tube. The difference in fibril lengths of the different regions may be viewed at the luminal surface of the tube or by examining a longitudinal wall cross section of the tube and looking at the different fibril lengths of the different regions at about the middle of the wall between the exterior and luminal surfaces. The exterior surface of the tube is considered to be the outer surface taken exclusive of the presence of any external reinforcing structures such as rings, spirals or ribs.

In another embodiment, the graft is constructed to be circumferentially distensible. This property enables the graft to be custom sized by the physician. It also enables the graft to be implanted with the maximum possible flow cross-sectional area for intraluminal placements. In yet another embodiment the benefits of distensibility can be maximized by providing resistance to recoil subsequent to increasing the circumference of the graft. This feature, as well, helps to ensure the maximum flow cross sectional area. The term circumference is used herein to describe the external boundary of a transverse cross section of the article of the present invention. For any given amount of distension, the circumference is the same whether the article is wrinkled, folded or smooth. No other form of radial reinforcement is known to be conducive to being rendered circumferentially distensible.

The radially supported regions are created by compressing regions of the graft longitudinally followed by localized heat treatment in that region. The heat treatment preserves the density increase in the region that results from the longitudinal compression. A wide variety of heat treatment methods including but not limited to induction, conduction, and convection can be used. Heated wires, lasers, and heated dies can be used to apply the thermal energy. Other suitable techniques can also be used.

The present invention may also be provided in other forms such as tapered tubes and sheets.

Alternatively, dense regions may be created by locally heat treating regions of tubular PTFE extrudate prior to expansion by stretching.

Intraluminal grafts and particularly the graft of the present invention may be used for in situ vascular bypass grafting as a means of holding open the leaflets of venous valves within a vein segment being used for the bypass. The various side branches or tributaries of the vein segment may also be occluded by the graft.

BRIEF DESCRIPTION OF THE DRAWINGS

FIG. 6 describes a scanning electron photomicrograph (×12) of a longitudinal cross section of the wall of the tube of the present invention.

FIGS. 7A and 7B describe respectively scanning electron photomicrographs (×500) of the longitudinal cross section of the wall and of the luminal surface of the tube of the present invention.

DETAILED DESCRIPTION OF THE INVENTION

The vascular graft of the present invention is preferably made from porous PTFE and most preferably porous PTFE having a microstructure of nodes interconnected by fibrils made as taught by U.S. Pat. Nos. 3,953,566 and 4,187,390, both of which are herein incorporated by reference. When comprised of porous PTFE, the vascular graft has additional utility because of the chemically inert character of PTFE and has particular value as an intraluminal graft placed within blood conduits including living arteries and veins, vascular bypass grafts, and various repairs to blood conduits. The pore size of the porous PTFE can be such that the graft is substantially impervious to leakage of blood and consequently does not require preclotting.

Figure 1:
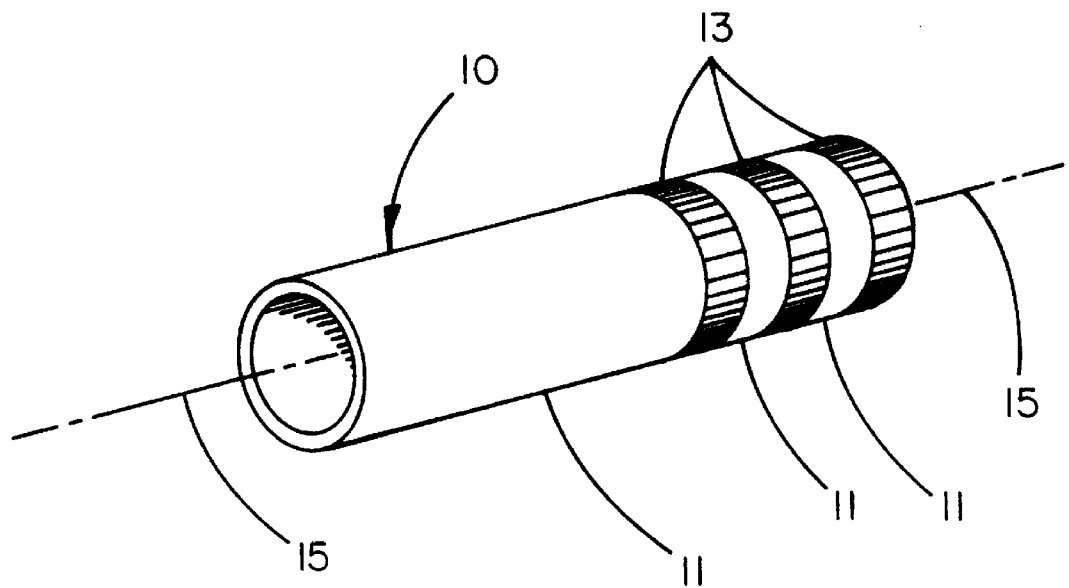
FIG. 1 describes a perspective view of a tube of the present invention having alternating regions of lesser and greater density in the form of ring shaped regions.

FIG. 1 describes an embodiment of the present invention wherein a porous PTFE tube 10 is provided with regions of lesser density 11 and regions of greater density 13. Preferably, the regions of lesser density 11 and regions of greater density 13 are in the form of adjacent, alternating ring-shaped regions. The denser ring-shaped regions provide the tube with a substantially greater degree of radial compression resistance than a graft in the form of a conventional tube of porous PTFE made which typically has walls made from only lesser density material.

FIG. 1 shows a tube having three ring-shaped regions of greater density 13 alternating with three regions of lesser density 11. While this figure describes a multiplicity of alternating lesser and greater density regions, it is apparent that as many alternating regions as desired may be provided. The invention requires that at least two regions of greater density are provided in some alternating relationship with at least two regions of lesser density. The regions of greater (or lesser) density need not be of uniform density nor need they be identically dense or extend completely around the circumference of the tube. Further, the regions may be of any width desired. For example, the regions of lesser density 11 may be of greater width (as measured in the direction of the longitudinal axis of the tube) than the width of the regions of greater density 13. Likewise, the width relationships may be reversed. It is also apparent that the individual regions of greater (or lesser) density are not required to be of equal width.

Figure 2:
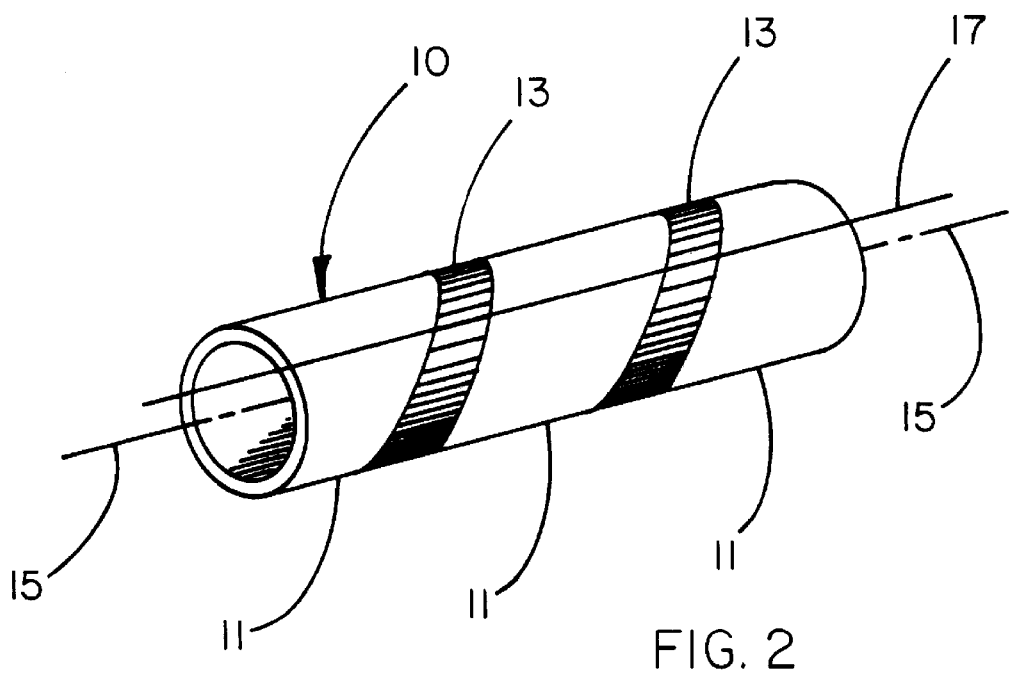
FIG. 2 describes a perspective view of a tube of the present invention wherein the alternating regions of lesser and greater density are provided in a spiral relationship.

Alternating regions of lesser density 11 and greater density 13 are defined as alternating (changing) from a region of one density to another density as one moves in one direction along any line along the outer surface of the tube 10 parallel to the longitudinal axis 15 of the tube 10. FIG. 2 describes an alternative embodiment wherein the regions of lesser density 11 and greater density 13 are provided in a spiral relationship. According to this embodiment, there is one region of lesser density 11 that spirals continuously around the tube 10 for the full length of the tube which alternates with one adjacent spiraling region of greater density 13. However, for the purposes of this invention, these regions are considered according to a hypothetical line 17 on the outer surface of the tube parallel to longitudinal axis 15. These individual continuous regions are therefore taken as two regions of greater density 13 alternating with three regions of lesser density 11.

Figure 3:
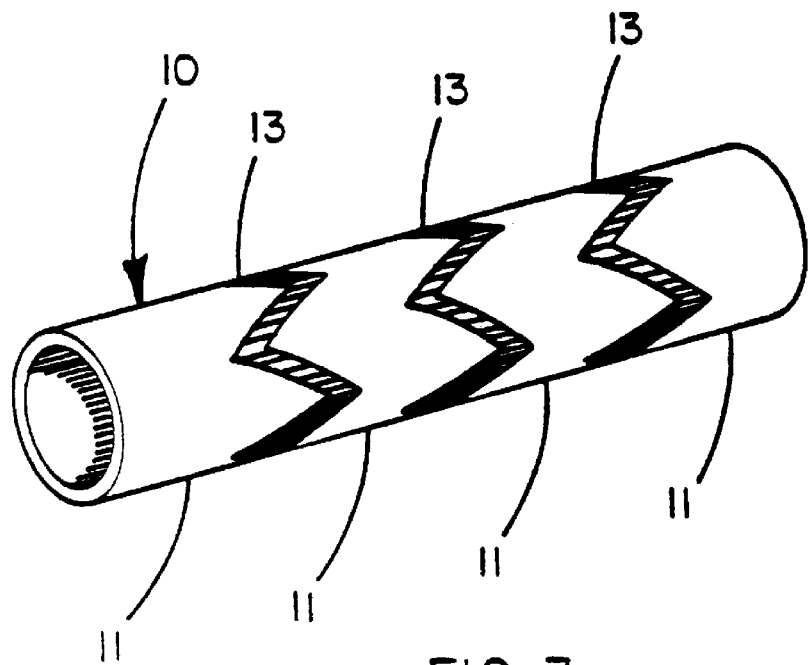
FIG. 3 describes a perspective view of an alternative embodiment to that of FIG. 1 wherein the different regions are provided in a zigzag or Z pattern.

As shown by FIG. 3, the regions of lesser density 11 and greater density 13 are not required to have generally straight boundaries. This figure describes an embodiment wherein the respective regions are generally ring-shaped in that they are generally oriented about the circumference of the tube 10 but wherein the regions are provided in a zigzag or "Z" pattern within the respective generally ring-shaped regions. As suggested by FIG. 3, it is apparent that the regions of alternating lesser density 11 and greater density 13 may be provided in any desired pattern. The different regions are not required to be in any uniform or symmetrical pattern.

FIGS. 1, 2 and 3 show the regions of greater density 13 shaded in a darker color than the regions of lesser density 11 in order to describe the invention. Porous expanded PTFE is conventionally a white, opaque material in which differences in density are not visually apparent unless they the regions are relatively large and the differences in density are substantial. Microscopy (preferably scanning electron microscopy) is generally required to visually identify the regions of different density. The difference in the regions is apparent to the touch if the regions are adequately large.

Figure 4:
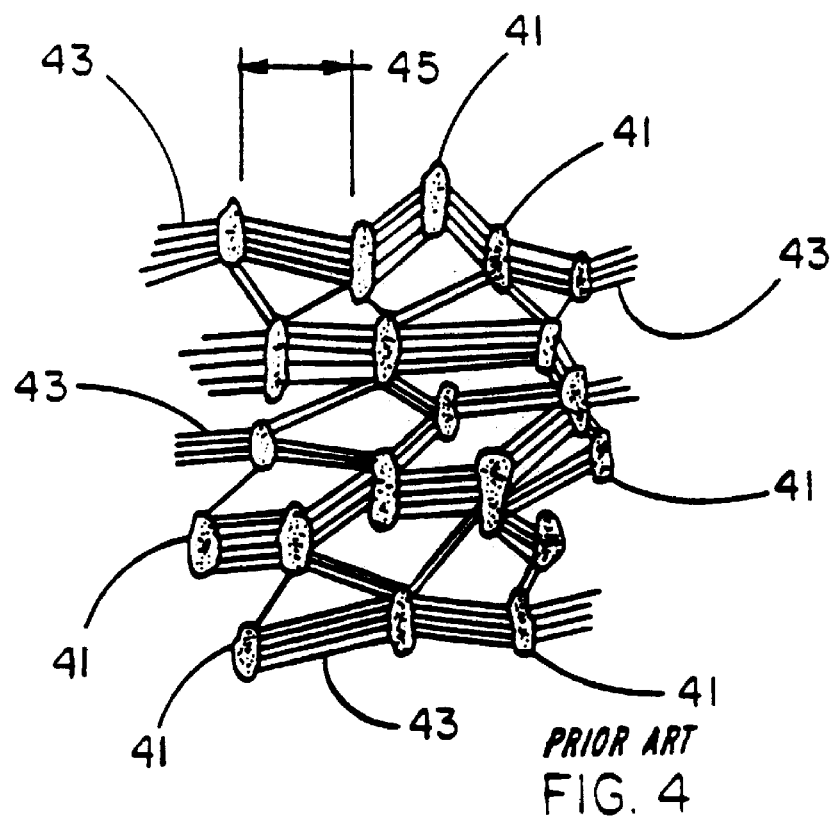
FIG. 4 describes a schematic representation of the microstructure of conventional porous PTFE of the prior art wherein nodes are interconnected by fibrils.
Figure 5:
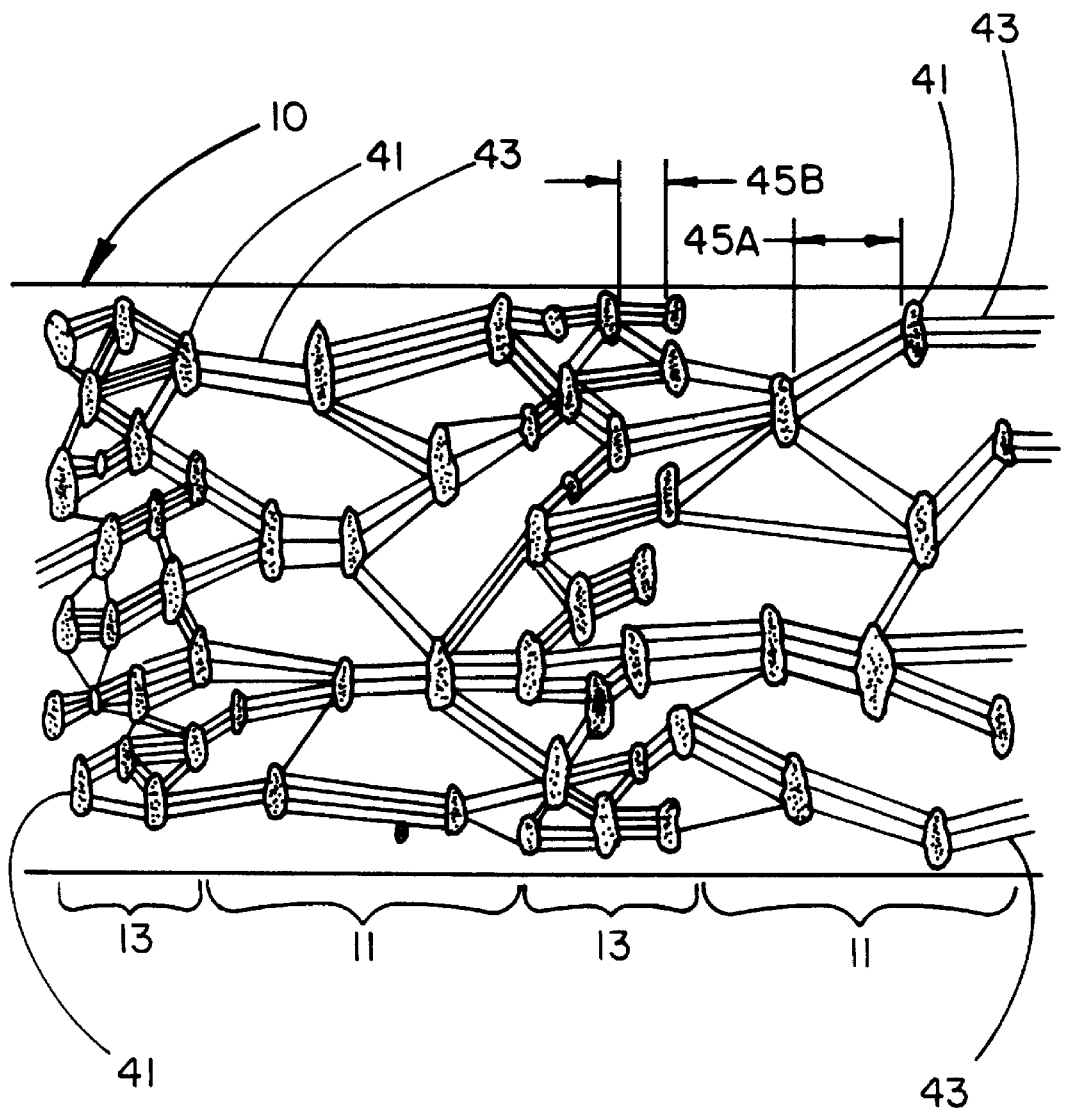
FIG. 5 describes a schematic representation of the microstructure of the tube of the present invention having alternating regions of lesser and greater density.

FIG. 4 describes a schematic representation of the microstructure of porous expanded PTFE made as taught by U.S. Pat. Nos. 3,953,566 and 4,187,390 to Gore wherein nodes 41 are interconnected by fibrils 43 with the fibrils generally oriented in the direction the material was stretched during manufacture. As will be further described the fibrils have a length 45 which is considered to be the distance as measured between the adjacent nodes in the predominant direction of the fibrils when the material is in a relaxed condition, i.e., not under any tension or compression. FIG. 5 describes the microstructure of the tube of the present invention showing how this microstructure is provided in regions of lesser density 11 and greater density 13 wherein the mean of the fibril lengths 45A of the region of lesser density 11 is longer than the mean of the fibril lengths 45B of the region of greater density 13. From this schematic representation, it is apparent that the region of lesser density 11 which has the relatively greater mean fibril length contains more void space than the region of greater density 13. This difference in void space obviously corresponds to the difference in density. Accordingly, a region is defined as a portion or segment of the material comprising the tube which has a relatively consistent fibril length. As described above, the present invention provides for at least two regions of lesser density 11 alternating with at least two regions of greater density 13. Preferably, the region of lesser density 11 has a mean fibril length which is at least 20% greater than the mean fibril length of the region of greater density 13. More preferably, the region of lesser density 11 has a mean fibril length 13 which is at least 50% greater than that of the region of greater density 13. Preferably region 13 has a bulk density which is at least 20% greater than that of region 11; it may be substantially greater such as 50% to 100%.

The schematic representation of FIG. 5 can be considered to be descriptive of the relative microstructure of the two regions of the invention as it appears at either the luminal surface of a tube and in a view of the wall of the tube as it would appear in a longitudinal cross section wherein the length of the fibrils (oriented parallel to the longitudinal axis of the tube) is in full view. The fibrils viewed in such a longitudinal cross section are at about the midpoint of the wall thickness; i.e., about halfway between the exterior and luminal surfaces, excluding external ribs.

While FIG. 5 describes a schematic view of the microstructure of the present invention showing straight fibrils, the fibrils may also be bent in various amounts. The microstructure of the present invention may optionally include substantially bent fibrils which can provide the tube with a degree of longitudinal rapid recovery as described by U.S. Pat. Nos. 4,877,661 and 5,308,664, also herein incorporated by reference.

The mean fibril lengths of the different regions of the tube of the present invention are determined from photomicrographs of either longitudinal cross sections of the tube wall or of the luminal surface of the tube. The mean fibril length was considered to be the average of ten measurements made in the predominant direction of the fibrils between nodes connected by fibrils. The ten measurements are made in the following manner. First, a photomicrograph is made of a representative region of the sample surface, of adequate magnification to show at least five sequential fibrils within the length of the photomicrograph. A series of five measurements are taken along a straight line drawn across the surface of the photomicrograph in the predominant direction of the fibrils followed by a second series of five measurements made along a second line drawn parallel to the first. A measurement constitutes the distance between adjacent nodes connected by at least one fibril. The ten measurements obtained by this method are averaged to obtain the mean fibril length of the region.

FIG. 6 describes a scanning electron photomicrograph showing both the luminal surface 61 and longitudinal cross sections of the wall 63 of a tube of the present invention wherein the cross section is taken along the length of the tube with the direction of viewing therefore perpendicular to the length. The different mean fibril lengths of the regions of lesser density 11 and greater density 13 are apparent. FIGS. 7A and 7B are scanning electron photomicrographs (×500) that respectively show views of the longitudinal wall cross section 63 and the luminal surface 61 of the same sample wherein these differences are also apparent. The three micrographs were taken of the nondistended article of Example 1. Following distension, the appearance was substantially the same. Samples were cut from a region of lesser density and another region of greater density and their respective bulk densities were determined according to the bulk volume and mass of the respective samples. For reference, the bulk density of non-porous PTFE is generally considered to be about 2.2 g/cc.

A preferred process for making a radially supported PTFE vascular graft of the present invention is sequentially described as follows. A longitudinally extruded and expanded porous PTFE tube is obtained and fitted coaxially over a stainless steel mandrel having an outside diameter the same as or slightly larger than the inside diameter of the porous PTFE tube. The ends of the tube are then pushed together so that the length of the tube is at least about 50%, and preferably about 20%, of the original length of the tube prior to this longitudinal compression. The tube and mandrel are then heated in an air convection oven set at 380° C. for approximately 50 seconds. Next, predetermined regions of the compressed tube are heat treated via the use of a laser. Subsequent to the laser treatment and cooling, the graft is removed from the mandrel. With moderate tension applied to the ends of the graft, the portions not treated by the laser extend out to their original length. The portions treated by the laser, however, are not readily extendible. These denser portions provide the radial support to the graft. The above process is described in steps 1 through 6 in the process flow chart depicted in FIG. 8.

Porous PTFE film can be helically wrapped onto the external surface of the tube and subsequently heat bonded to the tube at 380° C. for a sufficient period of time either prior to step 1 in FIG. 8 or the film can be applied after the tube has been laser treated, stripped from the mandrel, extended and refitted onto a mandrel of the same diameter. The film is made following the teachings of U.S. Pat. Nos. 3,953,566 and 4,187,390. This helically wrapped film provides hoop strength to the vascular graft, providing assurance against unacceptable aneurysmal dilatation. With the film so applied, the resulting graft is substantially non-distensible. Alternatively, a film wrapping may not be used thereby preserving the distensibility of the tube. Still another alternative is described in FIG. 8. Further processing the tube and creating a film tube as outlined in steps 7 through 13 of the flow chart provides a distensible, radially supported tube that can be subjected to internal pressure to circumferentially distend the tube up to a second circumference. With increasing pressure, the circumference changes very little beyond this second circumference; ultimately, the graft bursts without having dilated much beyond the second circumference. Film tube bonding, as described in step 9, and film tube bonding to the PTFE tube in step 12 are performed at 380° C.

Intraluminal radially supported grafts are preferably made to have a second circumference beyond which the circumference of the graft will not distend significantly unless the normal system operating pressure is substantially exceeded. For example, for an intraluminal graft, pressures in excess of 25 times normal human systolic blood pressure (120 mm Hg) may be required to cause the graft of the present invention to substantially increase in circumference beyond its second circumference. One embodiment of the blood conduit intraluminal graft would, for example, have an initial inside diameter of about 3 mm prior to circumferential distension. This small initial diameter allows for easy insertion into blood conduits. The second circumference of this embodiment would correspond to a diameter of, for example, 8 mm, so that the graft would be most useful for being inserted into blood conduits having inside diameters of up to about 8 mm. The second circumference for this embodiment, corresponding to an inside diameter of 8 mm, limits the further distension of the circumference of the blood conduit under virtually all normal operating conditions. The second circumference is established by the presence of the thin film tube of helically wrapped porous PTFE film. The film tube can be bonded to the outer surface of a substrate tube of porous PTFE. This substrate tube is preferably made by longitudinal extrusion and expansion whereby a seamless tube is created; alternatively, it is believed that the substrate tube may be made from a layer of porous PTFE film oriented substantially parallel to the longitudinal axis of a tube and having a seam in this same direction. The helically wrapped porous PTFE film is comprised primarily of fibrils which are oriented in the substantially circumferential direction around the outer surface of the substrate tube thereby restraining and limiting the second circumference of the resulting intraluminal graft. The helically wrapped porous PTFE film is preferably wrapped in multiple passes applied in opposing directions with respect to the longitudinal axis of the tube. It is believed that such an intraluminal graft may also be made from helically wrapped porous PTFE film wrapped helically in opposing directions without the use of a substrate tube. Conversely, the intraluminal graft may be made so as to not have a second circumference for applications not requiring additional circumferential strength, hence there is no pre-established limit to the circumferential growth of the graft.

Figure 8:
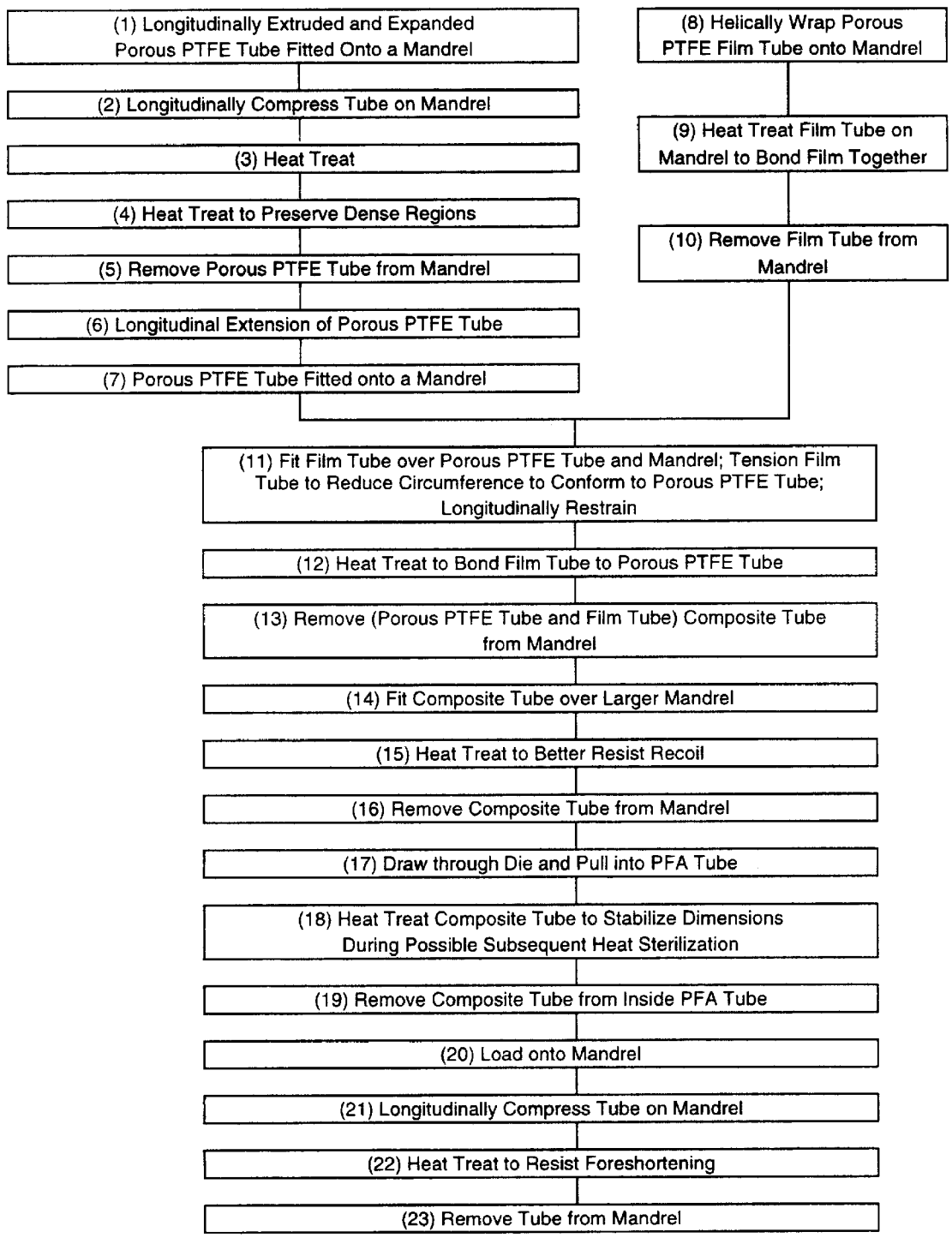
FIG. 8 describes sequential process steps for making articles of the present invention.

The distensible, radially supported tube as produced by following steps 1 through 13 of FIG. 8 can be further treated to provide resistance to recoil by completing steps 14 through 19. The heat treatment of step 15 serves to minimize tube recoil subsequent to circumferential distension. The heat treatment of step 18 serves to minimize dimensional changes associated with potential subsequent steam sterilization processes. These two heat treatment steps are performed at 380° C. and 200° C., respectively. Steps 20 through 23 minimize the foreshortening of the tube during subsequent circumferential distension.

The percentage recoil of a vascular graft is determined with the use of a tapered metal mandrel having a smooth, polished exterior surface. A suitable taper is 1.5° from the longitudinal axis. Preferably the mandrel is provided with incremental diameter graduations at intervals whereby the inside diameter of a tube may be determined by gently sliding a tube onto the smaller diameter end of the mandrel and allowing the tube to come to rest against the tapered mandrel surface and reading the appropriate graduation. Alternatively, the inside diameter of the tube may be measured by viewing the tube and mandrel, fitted together as previously described, using a profile projector measurement system. Using either a graduated mandrel or a profile projector, percentage recoil of a vascular graft is determined by first measuring the initial diameter of the graft. The graft is then gently slid further onto the tapered mandrel with a minimum of force until a diameter increase of 25% is obtained. This increased diameter is considered to be the distended diameter. The graft is then pushed from the mandrel avoiding the application of tension to the graft. After waiting at least 30 minutes to allow the graft to recoil, the recoil diameter is determined using the tapered mandrel by performing the same procedure as used to measure the initial diameter. Percentage recoil is then determined using the formula:

$$\frac{\text{Distended diameter} - \text{recoil diameter}}{\text{Distended diameter}} \times 100 = \% \text{ recoil}$$

Resistance to recoil is considered to mean articles exhibiting a percentage recoil value of 14% or less and more preferably 10% or less.

The laser treatment described in step 4 can be performed in a number of ways. The following parameters can be varied to provide tubes with varying degrees of kink and compression resistance. Ring, helical spiral and "Z" shaped patterns that extend completely around the tube, and combinations thereof can be applied to the tube via the use of the laser. Upon subsequent extension, the tube retains denser areas exhibiting the patterns. The patterns can also be applied by a variety of heat treatment processes including wrapping wires around the exterior of the tubes followed by heating the wire. The temperature chosen, the duration of the application of temperature, and the duty cycle of the application of thermal energy all are important process parameters. Changing these parameters results in varying degrees of thermal treatment. The process also can be modified to provide different heat treatment through the wall thickness of the tube. The compression resistance of the dense area can be modified by varying the degree of longitudinal compression in step 2 and by varying the width and spacing of the pattern.

The dense regions can be subjected to less thermal treatment so that the compressed material can be extended upon the application of moderate axial tension.

The graft may be manufactured to include a radiopaque substance if desired to visualize the graft after implantation into a living body. Radiopaque substances, barium sulfate for example, are well known to those skilled in the art of manufacturing various medical devices, such as indwelling catheters.

The graft may be implanted using conventional surgical techniques. Alternatively, using a catheter introducer, the graft may be introduced intraluminally into the vascular system and delivered via guidewire to the intended location, which may be a location remote from the point of insertion. It may be circumferentially distended at the intended location using a balloon catheter. The proximal end may be anchored by various means including stents, tissue adhesives, staples, or sutures. The distal end may be secured by the same methods, however, the conformability and resistance to recoil may allow the intraluminal graft to be used without being additionally secured at the distal end.

Furthermore, the radial support may be robust enough such that the graft need not be anchored in the case of intraluminal placement. That is, the graft may be circumferentially distended inside the host vessel to such a degree that frictional forces in the absence of significant graft recoil serve to adequately anchor the graft inside the host vessel.

The graft of the present invention is also anticipated to be particularly useful for in situ vascular bypass grafting procedures in which a vein is transected at the desired locations (thereby creating a vein segment) and reconnected into the arterial system, whereby the vein segment becomes an effective arterial bypass (e.g., in situ bypass grafting procedures wherein the vein segment is left in its original location). The saphenous vein is most typically used. The venous valves must be disrupted or rendered incompetent to prevent interference with arterial flow; likewise, all tributaries of the vein must be ligated or otherwise occluded so that the vein segment is entirely isolated from the venous system for use in its new arterial function. Venous valve disruption typically entails a valvulotomy wherein a valvulotome (a valve disrupting instrument) is inserted distally and advanced proximally through the entire length of the venous segment and then withdrawn, ideally disrupting the valve leaflets during withdrawal. The procedure is problematical due to the unreliability of the valvulotome in that it does not always entirely remove each valve, requiring that the procedure be repeated or risk leaving behind remnants of valve leaflets to accumulate thrombus. Likewise, there is attendant risk of damage to the lumen of the vein by the cutting edges of the valvulotome, particularly at tributaries. The side tributaries are typically occluded by individual surgical ligation. They are difficult to locate; most typically the leg must be opened for the entire length of the vein segment in order to assure that all tributaries have been occluded. This level of trauma results in increased time of operation and healing and increased risk of infection. Likewise, ligation of individual tributaries includes risk of omitting one or more tributaries with the attendant possibility of the creation of arterio-venous fistulas.

Intraluminal grafts are anticipated to provide an effective means of holding the leaflets of venous valves open in order to remove interference to arterial flow and likewise to provide an effective means of occluding tributaries. The intraluminal graft of the present invention is believed to be a preferred graft for this purpose; its porous, thin wall is anticipated to enhance biological compatibility for use with in situ procedures in comparison to previously available intraluminal graft materials.

Figure 9A:
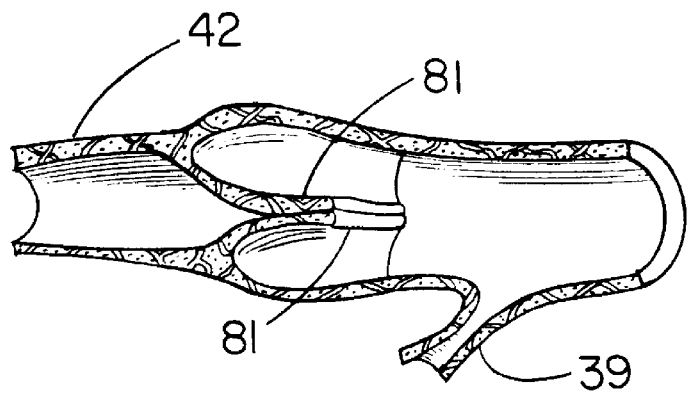
FIGS. 9A–9C are longitudinal cross sections that describe the use of the graft of the present invention to hold a venous valve open and occlude a tributary vessel.

FIG. 9A describes a perspective longitudinal cross section of a vein 42 showing the leaflets 81 of a typical bicuspid venous valve. Tributaries 39 occur at various locations along the length of a typical segment of a saphenous vein normally used for these procedures. A typical length of saphenous vein may include 5–12 tributaries and 2–5 venous valves which all require attention during an in situ procedure. Tributaries frequently occur immediately proximal to a venous valve as suggested by the figure.

Figure 9B:
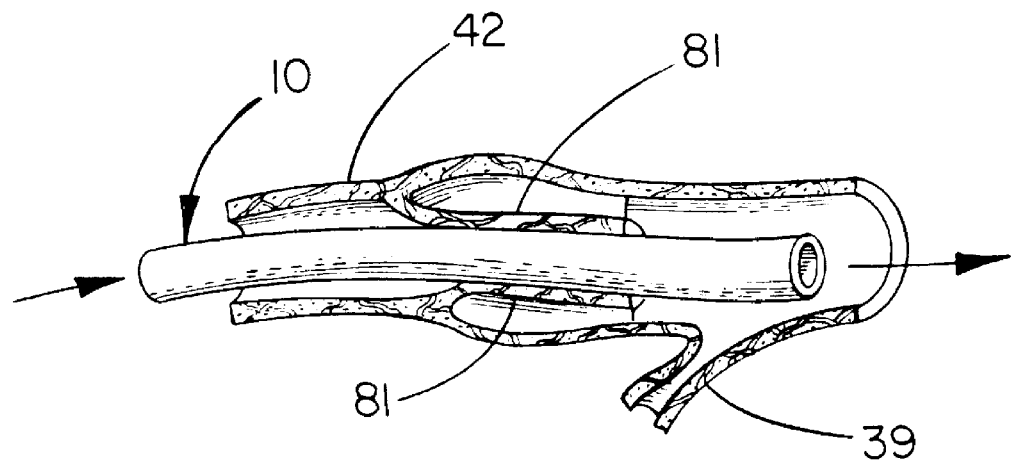
Figure 9C:
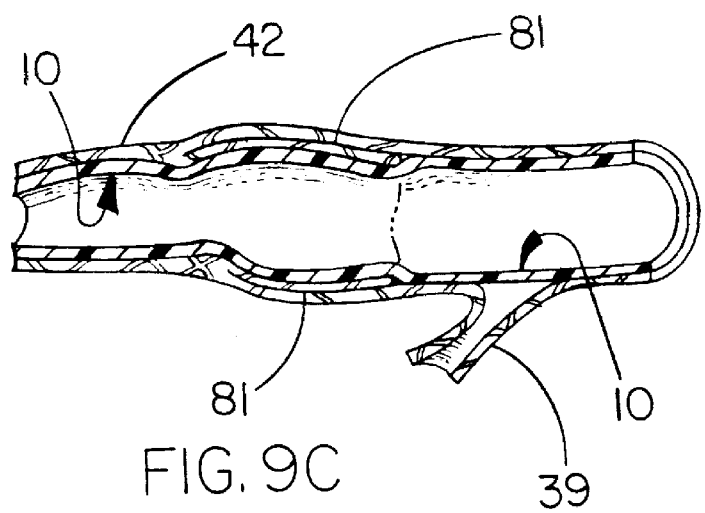

The intraluminal graft of the present invention may be fitted within a vein segment using methods previously described. When inserted into a vein segment and circumferentially distended against the vein wall as shown by FIGS. 9B and 9C, the intraluminal graft effectively holds the leaflets 81 of the venous valve open and also occludes tributaries 39. It accomplishes this in an effective manner without substantial risk of luminal damage to the vein and without the trauma related to individual ligation of tributaries. The risk of significant leaflet remnants remaining in the blood stream is eliminated. It is apparent that the intraluminal graft may be used in a continuous length suitable to line the entire length of the vein segment, occluding all tributaries and holding open all venous valves. Likewise, it is apparent that individual shorter segments of intraluminal graft may be used within the vein segment to individually address venous valves and/or tributaries if desired. Optionally, either or both ends of the intraluminal graft may be secured against the luminal wall of the vein segment by the use of one or more circumferentially distensible stents. If desired, a valvulotomy procedure may be performed to disrupt the valve leaflets prior to inserting the intraluminal graft into the vein segment. The intraluminal graft may also be used to repair damage to vein walls caused during a conventional valvulotomy wherein the graft provides a new luminal surface which covers the damaged regions of the walls.

EXAMPLE 1

A tube was made in accordance with the process steps outlined in the flowchart of FIG. 8. A substrate tube of step 1 was processed in accordance with the teachings of U.S. Pat. Nos. 3,953,566 and 4,187,390. The resulting tube possessed a 2.1 mm inner diameter and a 0.60 mm wall thickness. The tube was subjected to temperatures exceeding the crystalline melt point of PTFE in order to provide dimensional stability. The tube was placed over a 2.6 mm outer diameter mandrel and compressed longitudinally to about 20% of its initial length (step 2). All mandrels used in the examples were constructed of hollow Inconel® tubing (Huntington Alloys, Inc.). The tube on the mandrel was then placed for 42 seconds in an air convection oven set at 380° C. as per step 3.

Upon removal from the oven and cooling, with the tube still compressed longitudinally and secured on the mandrel, it was laser treated using model 2010, 20W CO 2 laser with a 6.35 mm focal length lens (Applied Laser Technology, Inc., Scottsdale, Ariz.). A clamping device and motor installed within the laser chamber enabled the tube to be rotated under the laser beam. The laser treatment consisted of the beam striking the surface of the tube, creating a ring around the circumference of specific sites along the length of the tube. The laser was operated in the proportional pulse mode with a pulse width of 300, and a pulse rate of 39999, while the graft was rotated at 600 revolutions per minute. The top of the graft was situated 9.4 cm below the reflecting mirror. The beam was set up to treat 0.7 mm wide regions with 1.6 mm wide gaps between the treated regions. This process was performed in accordance with step 4.

Per step 5, the tube was removed from the mandrel and extended under tension as per step 6 until the 1.6 mm wide gaps were increased in width to about 4.0 mm. The graft was reloaded onto a 2.6 mm outer diameter mandrel (per step 7) with its length extended to preserve the widths of the treated regions and the gaps.

As shown by step 8, 2.5 cm wide porous PTFE film manufactured in accordance with U.S. Pat. Nos. 3,953,566 and 4,187,390 was obtained and wrapped helically around a 10 mm outer diameter mandrel utilizing a 6.4 mm pitch. The film was helically applied in two passes of opposing direction. The film tube was heated per step 9 for 11 minutes in an air convection oven set at 380° C. Next, the film tube was removed from the mandrel (step 10). The film tube was placed coaxially over the porous PTFE tube of step 7. Tension was applied to the film tube in the longitudinal direction until the film tube fit snugly over the porous PTFE tube. Next, the film tube covered PTFE tube was longitudinally restrained, thereby completing step 11. Next, the mandrel containing the film tube and porous PTFE tube was placed for 9 minutes into an oven set at 380° C. in order to bond the film tube to the PTFE tube, per step 12.

The composite tube was then removed from the mandrel (step 13) and stretched in the radial direction by first pushing it onto the small end of a tapered mandrel having an outer diameter of 4 mm at one end and 6 mm at the other and then pushing it onto the 6 mm section of the mandrel; a short portion of the tube is left unstretched in order to facilitate later drawing through a die (step 14). The tube was maintained in a longitudinally compressed state throughout this step.

The composite tube was next heat treated to better provide resistance to recoil (step 15). The composite was placed for 3 minutes into an air convection oven set at 380° C. The composite tube was then removed from the mandrel (step 16) and subsequently pulled through a 3.8 cm long tapered die with an inner diameter of 8 mm at one end and an inner diameter of 4 mm at the other end; upon exiting the die the composite tube was pulled inside a 3.8 mm inner diameter perfluoro alkoxy resin (PFA) tube (step 17) in order to longitudinally and radially restrain the tube. The tube must be devoid of wrinkles. The graft within the PFA tube was placed into an air convection oven set at 200° C. for a period of 3 minutes (step 18). The composite graft was subsequently removed from the PFA tube (step 19) and loaded onto a mandrel having a 2.6 mm outer diameter (step 20). The composite tube was longitudinally compressed to approximately 75% of its original length and then restrained so it could not lengthen (step 21). The subsequent heat treatment for 10 minutes in an oven set at 200° C. served to reduce the amount of foreshortening of the tube during later circumferential distension. In the last step, step 23, the composite tube was removed from the mandrel.

Wall thickness, inner diameter, mean fibril length and density of the dense segment, mean fibril length and density of the region between dense regions, and compression resistance were measured for a tube constructed through step 23 and a tube so processed followed by subsequent circumferential distension accomplished by loading the tube onto a 6 mm outer diameter mandrel. The tube remained on the mandrel for about 60 seconds prior to removal. Wall thickness and inner diameter were measured using a tapered metal mandrel of round cross section and having a taper of about 1.5 degrees with respect to the longitudinal axis. The mandrel was provided with incremental graduations corresponding to various diameter increments. The tube diameter was determined by gently fitting an open end of the tube onto the small end of the tapered mandrel until the tube came to rest against the tapered surface of the mandrel, at which point the appropriate graduation was read. The wall thickness was determined by the use of a profile projector measurement system with the end of the tube still fitted to the tapered mandrel. Density was determined by cutting samples from the desired region, determining the bulk volume of the sample on the basis of its dimensions and a precise mass using a precision scale, and finally calculating the quotient of mass and volume. Mean fibril length was measured as described previously. The compression resistance tests were performed before and after distension at room temperature, under no internal pressure. Tubes were cut into 50 mm lengths and compressed between two 50 mm long by 30 mm wide plates parallel to each other using a tensile testing machine at a rate of 200 mm/min until the 50 mm long sections of the tubes were compressed by 1 mm. (1 mm compression corresponds to noticeable deflection of the tube circular cross section.). The test data appear in Table 1. Percentage recoil was measured for the tube not subjected to distension to be 4.4%. For comparison, the percentage recoil of a 3 mm thin wall Impra® Graft (product code IOS03TW, Impra, Inc., Tempe Ariz.) was determined to be 15.4%. The non-distended tube was also tested using the percentage recoil methodology except that the tube was not distended by 25%, rather it was distended to 6 mm. The resultant value was 5.0%. The distended tube was not tested for percentage recoil because it could not be effectively distended an additional 25%. Comparative data obtained from a commercially available 6 mm thin wall GORE-TEX® Vascular Graft (Item no. VT06080L) are also presented in the table. The mean fibril length and bulk density of this graft were 20 microns and 0.6 g/cc, respectively. This graft also could not be effectively distended 25%, hence percentage recoil is not reported.

The article of this example exhibited distensibility, resistance to recoil, and compression resistance greater than 400 g.

EXAMPLE 2

Another 6 mm thin wall tube was made with radial support, but not processed to be distensible. In this case the substrate tube was a commercially available GORE-TEX® Vascular Graft (Item No. VT06080L). The tube was processed in accordance with steps 2 through 6 of FIG. 8. The tube was placed over a 6 mm outer diameter mandrel and compressed longitudinally to about 27% of its initial length (step 2). The tube on the mandrel was then placed for 42 seconds in an air convection oven set at 380° C. as per step 3.

Upon removal from the oven and cooling, with the tube still compressed longitudinally and secured on the mandrel, it was laser treated using model 2010, 20W C02 laser with a 6.35 cm focal length lens (Applied Laser Technology, Inc., Scottsdale Ariz.). A clamping device and motor installed within the laser chamber enabled the tube to be rotated under the laser beam. The laser treatment consisted of the beam striking the surface of the tube, creating a ring around the circumference of specific sites along the length of the tube. The laser was operated in the proportional pulse mode with a pulse width of 400, and a pulse rate of 39999, while the graft was rotated at 600 revolutions per minute. The top of the graft was situated 9.4 cm below the reflecting mirror. The beam was set up to treat 0.7 mm wide regions with 1.6 mm wide gaps between the treated regions. This process was performed in accordance with step 4.

Per step 5, the tube was removed from the mandrel and extended under tension as per step 6 until the 1.6 mm wide gaps were increased in width to about 3.0 mm.

The test measurements were made in accordance with the procedures described above. All test data appear in Table 1. No percentage recoil value is reported for this tube because it could not be effectively distended 25%. The tube of this example exhibited compression resistance.

A similar tube comprised entirely of the material of the denser region of the article of this example (1.4 g/cc) is anticipated to have very poor handling and kink resistance characteristics, unlike the article of the present invention.

TABLE 1

|  | Example 1 Prior to Distension | Example 1 Subsequent to Distension | 6 mm Thin Walled GORE-TEX Vascular Graft | Example 2 |
|---|---|---|---|---|
| Wall Thickness (mm) | 0.59 | 0.55 | 0.39 | 0.44 |
| Inner Diameter (mm) | 3.6 | 5.7 | 5.9 | 6.0 |
| Mean Fibril Length (μm) Denser Region | 8.4 | 3.7 | — | 4.3 |
| Mean Fibril Length (μm) Less Dense Region | 16 | 17 | — | 17 |

TABLE 1-continued

|  | Example 1 Prior to Distension | Example 1 Subsequent to Distension | 6 mm Thin Walled GORE-TEX Vascular Graft | Example 2 |
|---|---|---|---|---|
| Bulk Density (g/cc) Denser Region | 1.0 | 1.0 | — | 1.4 |
| Bulk Density (g/cc) Less Dense Region | 0.7 | 0.7 | — | 0.7 |
| Compression Resistance (g) | 994 | 1007 | 89 | 906 |
| Percentage Recoil (%) | 4.4 | — | — | — |

We claim:

1. A method of performing an in situ bypass, comprising:
   a. transecting a vein to form a vein segment;
   b. inserting a circumferentially distensible intraluminal graft into the vein segment and into at least one venous valve within the vein segment;
   c. circumferentially distending the intraluminal graft, thereby holding open the at least one venous valve; and
   d. anastomosing the vein segment to adjacent arteries;
   wherein the intraluminal graft comprises a porous PTFE tube having a microstructure of nodes interconnected by fibrils, said tube having a luminal surface, at least two first regions and two second regions wherein said second regions have a greater mean fibril length than said first regions when fibril lengths are measured at the luminal surface of the tube.

2. A method of holding leaflets of a venous valve in an open condition, comprising inserting a circumferentially distensible intraluminal graft into a segment of a vein and into a venous valve within the vein, and circumferentially distending the intraluminal graft, thereby holding open the leaflets of the venous valve, wherein the intraluminal graft comprises a porous PTFE tube having a microstructure of nodes interconnected by fibrils, said tube having a luminal surface, at least two first regions and two second regions having fibril lengths wherein said second regions have a greater mean fibril length than said first regions when fibril lengths are measured at the luminal surface of the tube.

3. A method according to claim 1 wherein the intraluminal graft occludes at least one tributary branch of the venous segment.

4. A method according to claim 2 wherein the intraluminal graft occludes at least one tributary branch of the venous segment.

* * * * *